United States Patent
Yasohara et al.

(12) 
(10) Patent No.: US 6,214,610 B1
(45) Date of Patent: Apr. 10, 2001

(54) PROCESS FOR THE PREPARATION OF OPTICALLY ACTIVE N-BENZYL-3-PYRROLIDINOL

(75) Inventors: Yoshihiko Yasohara, Himeji; Junzo Hasegawa, Akashi, both of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/308,754

(22) PCT Filed: Nov. 26, 1997

(86) PCT No.: PCT/JP97/04299

§ 371 Date: Jun. 28, 1999

§ 102(e) Date: Jun. 28, 1999

(87) PCT Pub. No.: WO98/23768

PCT Pub. Date: Jun. 4, 1998

(30) Foreign Application Priority Data

Nov. 26, 1996 (JP) .................................................... 8-331467

(51) Int. Cl.[7] .................................................. C12D 17/10
(52) U.S. Cl. ............................................. 435/280; 435/121
(58) Field of Search ...................................... 435/280, 121

(56) References Cited

FOREIGN PATENT DOCUMENTS 6-141876 * 5/1994 (JP) .

OTHER PUBLICATIONS

ATCC Yeasts, 19th Edition, 1995, pp. 30, 56, 61,65, 123, 131.*

* cited by examiner

Primary Examiner—Sandra E. Saucier
(74) Attorney, Agent, or Firm—Connolly Bove Lodge & Hutz LLP

(57) ABSTRACT

The invention provides an efficient method of producing optically active N-benzyl-3-pyrrolidinol by an enzymatic reaction stereoselectively reducing N-benzyl-3-pyrrolidinone.

The invention consists in a method of producing optically active N-benzyl-3-pyrrolidinol which comprises a step of obtaining a reaction mixture by treating N-benzyl-3-pyrrolidinone with cells or a culture of a microorganism, or a material derived therefrom, and a step of recovering optically active N-benzyl-3-pyrrolidinol from said reaction mixture, in which method said microorganism mentioned above is a microorganism belonging to the genus Dipodascus, Debaryomyces, Cryptococcus, Pichia, Rhodosporidium, Trichosporon, Micrococcus, Komagataella, Ogataea or Zygosaccharomyces.

3 Claims, No Drawings

PROCESS FOR THE PREPARATION OF OPTICALLY ACTIVE N-BENZYL-3-PYRROLIDINOL

TECHNICAL FIELD

The present invention relates to a method of producing optically active N-benzyl-3-pyrrolidinol, which is useful as an intermediate for the synthesis of medicinal compounds such as β-lactam antibiotics and dihydropyridine compounds.

BACKGROUND ART

Optically active N-benzyl-3-pyrrolidinol is useful as an intermediate for the synthesis of medicinal compounds. For the method of producing optically active N-benzyl-3-pyrrolidinol, a technology comprising synthesizing the same from an optically active compound and a technology starting with a prochiral compound and conducting asymmetric synthesis or optical resolution, among others, are known. As such a method, the method disclosed in Japanese Kokai Publication Hei-06-141876 comprises producing optically active N-benzyl-3-pyrrolidinol by stereoselectively reducing N-benzyl-3-pyrrolidinone in the presence of an enzyme capable of catalyzing the stereoselective reduction of N-benzyl-3-pyrrolidinone. However, this method is not suited for practical use, partly because fungi used as an enzyme source are difficult to cultivate on an industrial scale and carry out the process thereafter and partly because the charge concentration of the substrate and the rate of conversion from the substrate to the product are low.

SUMMARY OF INVENTION

In view of the foregoing, it is an object of the present invention to provide an efficient method of producing optically active N-benzyl-3-pyrrolidinol by an enzymatic reaction involving stereoselective reduction of N-benzyl-3-pyrrolidinone.

The present invention consists in a method of producing optically active N-benzyl-3-pyrrolidinol which comprises a step of obtaining a reaction mixture by treating N-benzyl-3-pyrrolidinone with cells or a culture of a microorganism, or a material derived therefrom, and a step of recovering optically active N-benzyl-3-pyrrolidinol from said reaction mixture, in which method said microorganism is a microorganism belonging to the genus Dipodascus, Debaryomyces, Cryptococcus, Pichia, Rhodosporidium, Trichosporon, Micrococcus, Komagataella, Ogataea or Zygosaccharomyces.

DETAILED DESCRIPTION OF THE INVENTION

In the following, the present invention is described in detail.

In the present invention, the substrate N-benzyl-3-pyrrolidinone is first treated with cells or a culture of the microorganism, or a material derived therefrom, to give a reaction mixture.

Said N-benzyl-3-pyrrolidinone can be synthesized by the process disclosed in Japanese Kokai Publication Sho-54-16466. Thus, benzylamine and ethyl acrylate are subjected to Michael addition and the thus-obtained β-alanine derivative is reacted with ethyl chloroacetate in the presence of a base. The compound obtained is cyclized in the presence of metallic sodium to give N-benzyl-4-carboethoxy-3-pyrrolidone, which is decarboxylated by using hydrochloric acid, whereby N-benzyl-3-pyrrolidinone can be obtained.

In the present invention, a microorganism belonging to the genus Dipodascus, Debaryomyces, Cryptococcus, Pichia, Rhodosporidium, Trichosporon, Micrococcus, Komagataella, Ogataea or Zygosaccharomyces is used as the above-mentioned microorganism. Such a microorganism stereoselectively reduces the 3-position carbonyl group of the above-mentioned N-benzyl-3-pyrrolidinone.

Specific examples of said microorganism include, but are not particularly limited to, Dipodascus tetrasperma CBS 765.70, Debaryomyces hansenii var. hansenii IFO 0728, Cryptococcus albidus var. albidus IFO 0378, Pichia membranaefaciens IFO 0189, Rhodosporidium toruloides IFO 0413, Trichosporon fermentans ATCC 10675, Micrococcus luteus IFO 13867, Komagataella pastoris IFO 0948, Ogataea polymorpha IFO 1476, Zygosaccharomyces bailii IFO 0519 and the like.

These microorganisms can be obtained from stock cultures which are readily available or purchasable. They can also be isolated from the natural world. It is also possible to obtain microbial strains having properties advantageous to the present reaction by causing mutation in these microorganisms. Further, those derived from these microorganisms by the genetic engineering or bioengineering techniques, such as recombinant DNA and cell fusion etc., may also be used.

Said microorganisms can be cultivated by using a medium containing nutrient components. A solid medium such as an agar medium or a liquid medium is generally used as said medium. For mass cultivation of said microorganism, a liquid medium is suitably used. The carbon source, for example, saccharides such as glucose, sucrose and maltose, organic acids such as lactic acid, acetic acid and citric acid, alcohols such as ethanol and glycerol, and mixtures of these can be incorporated in the medium, and the nitrogen source, for example, ammonium sulfate, ammonium phosphate, urea, yeast extracts, meat extracts, peptone and the like can be incorporated. Further, other inorganic salts, vitamins and other nutrient sources may also be incorporated optionally.

Said microorganisms can be cultivated generally under ordinary conditions, for example aerobically at pH 4.0 to 9.5 within the temperature range of 20 to 45° C. for 10 to 96 hours.

In treating the above-mentioned N-benzyl-3-pyrrolidinone with the above-mentioned microorganisms, the culture fluid containing said microorganism as obtained can generally be used. In cases, however, a component in the culture fluid interferes the reaction, the use of a suspension obtained by treating said culture fluid by centrifugation, for instance, is preferred.

The materials derived from cells of said microorganisms include, but are not particularly limited to, dried cells, materials obtained from the cells by treatment with a surfactant or an organic solvent, and materials obtained by treating the cells with a lytic enzyme. Furthermore, enzyme preparations prepared by extraction from the cells or cultures can also be used.

The material derived from the culture includes, but is not particularly limited to, concentrated cultures, dried cultures, surfactant- or organic solvent-treated cultures, lytic enzyme-treated cultures and the like. Furthermore, enzyme preparations purified from the cultured cells or cultures may also be used.

In carrying out the reaction by treating the above-mentioned N-benzyl-3-pyrrolidinone with the above-mentioned microbial cells, cultures or materials derived therefrom, said N-benzyl-3-pyrrolidinone may be added all once at initially or in portions. The reaction temperature on that case is generally 15 to 50° C., preferably 20 to 40° C., and the pH is 2.5 to 9.0.

The amount of the cells in the reaction mixture may suitably be selected depending on the catalysing ability of the cells. The substrate concentration is preferably 0.01 to 50% (w/v), more preferably 0.1 to 20% (w/v).

Generally, the reaction is carried out with shaking or with aeration and agitation. The reaction time may suitably be selected depending on the substrate concentration, the amount of microorganism and other reaction conditions. Generally, it is preferred that the respective conditions be selected so that the reaction may be complete in 2 to 168 hours. For promoting the above reaction, an energy source such as glucose can be added to the reaction mixture in an amount of 1 to 5%, whereby good results may be obtained.

Further, the reaction can be promoted by adding a coenzyme component, such as reduced form nicotinamide adenine dinucleotide (NADH) or reduced form nicotinamide adenine dinucleotide phosphate (NADPH), which is generally deemed necessary for reduction reactions in biological processes. In the concrete, either these may be added to the reaction system, or a reaction system capable of forming NADH, NADPH or the like may be added to the reaction system. For example, use may be made of the reaction by which NADH is formed from NAD on the occasion of the formation of carbon dioxide and water from formic acid in the presence of formate dehydrogenase, or the reaction by which NADH/NADPH is formed from NAD/NADP on the occasion of the formation of gluconolactone from glucose in the presence of glucose dehydrogenase. A surfactant such as Triton (product of Nakalai Tesque), Span (product of Kanto Chemical) or Tween (product of Nakalal Tesque) may also be added.

In the present reaction, the product, namely optically active N-benzyl-3-pyrrolidinol, is then recovered from the reaction mixture.

The method of recovering said N-benzyl-3-pyrrolidinol from the reaction mixture is not particularly restricted but any general method of isolation may be employed. For example, optically active N-benzyl-3-pyrrolidinol can be obtained by a method which comprises adding an organic solvent such as ethyl acetate to the reaction mixture to thereby effect extraction, dehydrating the obtained extract over anhydrous sodium sulfate or the like, and removing the organic solvent under reduced pressure. In this case, a salt such as sodium hydrogen carbonate or sodium chloride may be added to improve the extraction efficiency. When necessary, this roughly purified product can be converted to a more purified form of optically active N-benzyl-3-pyrrolidinol by distillation, silica gel column chromatography or the like technique.

BEST MODES FOR CARRYING OUT THE INVENTION

The following examples illustrate the present invention in further detail. They are, however, by no means limitative of the scope of the present invention.

EXAMPLE 1

A liquid medium having the composition shown below was prepared and distributed in 5-ml portions into large-sized test tubes and steam-sterilized at 120° C. for 20 minutes.

| Medium composition: | |
|---|---|
| Glucose | 4% |
| Yeast extract | 0.3% |
| $KH_2PO_4$ | 0.1% |
| $(NH_4)_2HPO_4$ | 0.65% |
| NaCl | 0.1% |
| $MgSO_4.7H_2O$ | 0.8% |
| $ZnSO_4.7H_2O$ | 0.06% |
| $FeSO_4.7H_2O$ | 0.09% |
| $CuSO_4.5H_2O$ | 0.005% |
| $MnSO_4.4{\sim}6H_2O$ | 0.01% |
| Tap water | |
| pH 7.0 | |

Those medium portions were respectively inoculated with one loopful of one of the microorganisms shown in Table 2. Then, shake culture was conducted at 30° C. for 24 to 72 hours. Thereafter, cells were harvested from each culture fluid by centrifugation, washed with water and then suspended in 1 ml of 100 mM phosphate buffer (pH 6.5). Each suspension was used as a component of the following reaction mixture.

| | Reaction mixture composition: | |
|---|---|---|
| (1) | The above cell suspension | 1 ml |
| (2) | Glucose | 20 mg |
| (3) | N-Benzyl-3-pyrrolidinone | 10 mg |

The above components (1) to (3) distributed into each test tube were mixed up and the reaction was allowed to proceed at 30° C. with shaking for 20 hours. After the reaction, 3.5 ml of ethyl acetate was added to each reaction mixture and the whole was stirred well. A portion of the organic layer was subjected to gas chromatography and assayed for N-benzyl-3-pyrrolidinol content. The optical purity thereof was also determined by HPLC.

Gas chromatography conditions: column: Uniport B, 10% PEG-20M, 4.0 mm ID×1.0 m; column temperature: 200° C.; carrier gas: nitrogen; detection: FID.

HPLC analysis conditions: column: Chiralcel OB (product of Daicel Chemical Industries); eluent: n-hexane/isopropanol/diethylamine =99/1/0.1; detection: 254 nm; flow rate: 1 ml/min.; elution time: (R) form 6.1 minutes, (S) form 7.9 minutes.

The rates of conversion to product and the optical purities of the products are summarized in Table 1.

TABLE 1

| Microbial strain | Conversion Rate (%) | Optical purity (% ee) |
|---|---|---|
| *Dipodascus tetrasperma* CBS 765.70 | 10 | (S) 97 |
| *Debaryomyces hansenii* var. *hansenii* IFO 0728 | 7 | (S) 84 |
| *Cryptococcus albidus* var. *albidus* IFO 0378 | 34 | (S) 100 |
| *Pichia membranaefaciens* IFO 0189 | 12 | (S) 84 |
| *Rhodosporidium toruloides* IFO 0413 | 33 | (S) 74 |
| *Trichosporon fermentans* ATCC 10675 | 75 | (S) 96 |

TABLE 1-continued

| Microbial strain | Conversion Rate (%) | Optical purity (% ee) |
| --- | --- | --- |
| Komagataella pastoris IFO 0948 | 14 | (S) 61 |
| Ogataea polymorpha IFO 1476 | 17 | (S) 89 |
| Zygosaccharomyces bailii IFO 0519 | 12 | (S) 62 |

EXAMPLE 2

A liquid medium having the composition shown below was prepared and distributed in 10-ml portions into large-sized test tubes and steam-sterilized at 120° C. for 20 minutes.

| Medium composition: | |
| --- | --- |
| Meat extract | 1.0% |
| Peptone | 1.0% |
| Yeast extract | 0.5% |
| NaCl | 0.3% |
| Tap water | |
| pH 7.0 | |

Each portion of this liquid medium was inoculated with one loopful of *Micrococcus luteus* IFO 13867 and shake culture was performed at 30° C. for 24 hours. Then, this culture fluid was subjected to centrifugation and cells were thereby harvested, washed with water, and suspended in 2 ml of 100 mM phosphate buffer (pH 6.5) and the suspension was used as a component of the reaction mixture in the same manner as in Example 1. After allowing the reaction to proceed for 20 hours, the rate of conversion to product and the optical purity of the product were determined in the same manner as in Example 1. The conversion rate was 81% and the optical purity was (S) 100% ee.

EXAMPLE 3

The microorganisms indicated in Table 3 were cultured in the same manner as in Example 1. Then, each culture fluid was subjected to centrifugation to thereby harvest cells, which were washed with water and suspended in 1 ml of 100 mM phosphate buffer (pH 6.5). The suspension was used as a component of the following reaction mixture.

| | Reaction mixture composition: | |
| --- | --- | --- |
| (1) | The above cell suspension | 0.5 ml |
| (2) | Glucose | 5.4 mg |
| (3) | Nicotinamide adenine dinucleotide phosphate (oxidized form) | 0.275 mg |
| (4) | Glucose dehydrogenase (product of Amano Pharmaceutical) | 2.84 units |
| (5) | N-Benzyl-3-pyrrolidinone | 1 mg |

The above components (1) to (5) were placed in a test tube and mixed up, and the reaction was allowed to proceed at 30° C. with shaking for 20 hours. After the reaction, the rate of conversion to product and the optical purity of the product were determined in the same manner as in Example 1. The results thus obtained are summarized in Table 2.

TABLE 2

| Microbial strain | Conversion rate (%) | Optical purity (% ee) |
| --- | --- | --- |
| Dipodascus tetrasperma CBS 765.70 | 15 | (S) 96 |
| Debaryomyces hansenii var. hansenii IFO 0728 | 9 | (S) 84 |
| Cryptococcus albidus var. albidus IFO 0378 | 47 | (S) 91 |
| Pichia membranaefaciens IFO 0189 | 61 | (S) 83 |
| Rhodosporidium toruloides IFO 0413 | 74 | (S) 76 |
| Trichosporon fermentans ATCC 10675 | 74 | (S) 96 |
| Komagataella pastoris IFO 0948 | 18 | (S) 58 |
| Ogataea polymorpha IFO 1476 | 13 | (S) 89 |
| Zygosaccharomyces bailii IFO 0519 | 15 | (S) 58 |

EXAMPLE 4

The microorganisms indicated in Table 3 were cultured in the same manner as in Example 1. Then, each culture fluid was subjected to centrifugation to thereby harvest cells, which were washed with water and suspended in 1 ml of 100 mM phosphate buffer (pH 6.5). The suspension was used as a component of the following reaction mixture.

| | Reaction mixture composition: | |
| --- | --- | --- |
| (1) | The above cell suspension | 0.5 ml |
| (2) | Glucose | 5.4 mg |
| (3) | Nicotinamide adenine dinucleotide (oxidized form) | 0.26 mg |
| (4) | Glucose dehydrogenase (product of Amano Pharmaceutical) | 2.84 units |
| (5) | N-Benzyl-3-pyrrolidinone | 1 mg |

The above components (1) to (5) were placed in a test tube and mixed up, and the reaction was allowed to proceed at 30° C. with shaking for 20 hours. After the reaction, the rate of conversion to product and the optical purity of the product were determined in the same manner as in Example 1. The results thus obtained are summarized in Table 3.

TABLE 3

| Microbial strain | Conversion rate (%) | Optical purity (% ee) |
| --- | --- | --- |
| Dipodascus tetrasperma CBS 765.70 | 33 | (S) 99 |
| Debaryomyces hansenii var. hansenii IFO 0728 | 6 | (S) 83 |
| Pichia membranaefaciens IFO 0189 | 24 | (S) 80 |
| Rhodosporidium toruloides IFO 0413 | 72 | (S) 76 |
| Trichosporon fermentans ATCC 10675 | 74 | (S) 96 |
| Komagataella pastoris IFO 0948 | 19 | (S) 59 |
| Ogataea polymorpha IFO 1476 | 11 | (S) 87 |
| Zygosaccharomyces bailii IFO 0519 | 13 | (S) 63 |

EXAMPLE 5

*Micrococcus luteus* IFO 13867 was cultured in the same manner as in Example 2. The cells obtained were suspended in 2 ml of 100 mM phosphate buffer (pH 6.5), and the suspension was used as a component of the reaction mixture given in Example 3. After allowing the reaction to proceed for 20 hours, the rate of conversion to product and the optical purity of the product were determined in the same manner as in Example 1. The conversion rate was 78% and the optical purity was (S) 100% ee.

EXAMPLE 6

*Micrococcus luteus* IFO 13867 was cultured in the same manner as in Example 2. The cells obtained were suspended in 2 ml of 100 mM phosphate buffer (pH 6.5), and the suspension was used as a component of the reaction mixture given in Example 4. After allowing the reaction to proceed for 20 hours, the rate of conversion to product and the optical purity of the product were determined in the same manner as in Example 1. The conversion rate was 78% and the optical purity was (S) 100% ee.

EXAMPLE 7

A liquid medium having the composition given in Example 2 was prepared and distributed in 100-ml portions into twenty-five 500-ml Sakaguchi flasks and steam-sterilized at 120° C. for 20 minutes. The contents of each flask was aseptically inoculated with 2 ml of a fluid culture obtained by cultivating *Micrococcus luteus* IFO 13867 in the same manner as in Example 2, and shake-culture was carried out at 30° C. for 24 hours. Cells were harvested from the resultant culture fluids by centrifugation and suspended in 500 ml of 100 mM phosphate buffer (pH 6.5). To this suspension was added 5 g of N-benzyl-3-pyrrolidinone, and 10 g of glucose. The reaction was allowed to proceed at 30° C. with stirring for 24 hours, while the reaction mixture wag maintained at pH 6.5 with 6N aqueous sodium hydroxide solution. Thereafter, the reaction mixture was extracted with 2.5 L of ethyl acetate, and the aqueous layer was further extracted with 1 L of ethyl acetate. The organic layers were combined and dehydrated over anhydrous sodium sulfate, and the solvent was then distilled off under reduced pressure. The residue was distilled to give 3 g of (S)-N-benzyl-3-pyrrolidinol. The yield was 60%, the optical purity was 99.8% ee, the boiling point was 132 to 137° C./3 mm Hg, and the optical rotation $[\alpha]_D^{20}$ was -3.77° ($CH_3OH$, c=5). $^1$H-NMR δ ($CDCl_3$): 1.63–1.76 (1H, m), 2.09–2.21 (1H, m), 2.26–2.37 (1H, m), 2.51–2.64 (2H, m), 2.75–2.85 (1H, m), 3.38 (1H, brs), 3.61 (2H, s), 4.24–4.33 (1H, m), 7.19–7.37 (5H, m).

EXAMPLE 8

A liquid medium having the composition given in Example 1 was prepared and distributed in 50-ml portions into fifty 500-ml Sakaguchi flasks and steam-sterilized at 120° C. for 20 minutes. The contents of each flask was aseptically inoculated with 1 ml of a fluid culture obtained by cultivating *Trichosporon fermentans* ATCC 10675 in the same manner as in Example 1, and shake-culture was carried out at 30° C. for 24 hours. Cells were harvested from the resultant culture fluids by centrifugation and suspended in 500 ml of 100 mM phosphate buffer (pH 6.5). To this suspension, there were added 5 g of N-benzyl-3-pyrrolidinone, 10 g of glucose, 275 mg of oxidized form nicotinamide adenine dinucleotide phosphate (product of Kohjin Co.) and 1,420 units of glucose dehydrogenase (product of Amano Pharmaceutical Co.), and the reaction was allowed to proceed at 30° C. with stirring for 48 hours, while the reaction mixture was maintained at pH 6.5 with 6N aqueous sodium hydroxide solution. Thereafter, the reaction mixture was extracted with 2.5 L of ethyl acetate, and the aqueous layer was further extracted with 1 L of ethyl acetate. The organic layers were combined and dehydrated over anhydrous sodium sulfate, and the solvent was then distilled off under reduced pressure. The residue was purified by subjecting the same to silica gel column chromatography (eluent: ethyl acetate/methanol=2/1) to give 2.5 g of (S)-N-benzyl-3-pyrrolidinol. The yield was 49%, the optical purity was 96% ee, the boiling point was 132 to 137° C./3 mm Hg, and the optical rotation $[\alpha]_D^{20}$ was -3.73° ($CH_3OH$, c=5). $^1$H-NMR δ $CDCl_3$): 1.63–1.76 (1H, m), 2.09–2.21 (1H, m), 2.26–2.37 (1H, m), 2.51–2.64 (2H, m), 2.75–2.85 (1H, m), 3.38 (1H, brs), 3.61 (2H, s), 4.24–4.33 (1H, m), 7.19–7.37 (5H, m).

EXAMPLE 9

A liquid medium having the composition given in Example 1 was prepared and distributed in 50-ml portions into fifty 500-ml Sakaguchi flasks and steam-sterilized at 120° C. for 20 minutes. The contents of each flask was aseptically inoculated with 1 ml of a fluid culture obtained by cultivating *Trichosporon fermentans* ATCC 10675 in the same manner as in Example 1, and shake-culture was carried out at 30° C. for 24 hours. Cells were harvested from the resultant culture fluids by centrifugation and suspended in 500 ml of 100 mM phosphate buffer (pH 6.5). The cells were disrupted by a Brown cell disrupter under ice cooling, and the supernatant obtained by centrifugation, namely the cell-free extract, was used as a component of the following reaction mixture.

| Reaction mixture composition: | | |
| --- | --- | --- |
| (1) | The above cell suspension | 0.5 ml |
| (2) | Glucose | 5.4 mg |
| (3) | Nicotinamide adenine dinucleotide (oxidized form) | 0.26 mg |
| (4) | Glucose dehydrogenase (product of Amano Pharmaceutical) | 2.84 units |
| (5) | N-Benzyl-3-pyrrolidinone | 1 mg |

The above components (1) to (5) were placed in a test tube and mixed up, and the reaction was allowed to proceed at 30° C. with shaking for 20 hours. After the reaction, the rate of conversion to product and the optical purity of the product were determined in the same manner as in Example 1. The conversion rate was 19% and the optical purity was (S) 96% ee.

INDUSTRIAL APPLICABILITY

The method of producing optically active N-benzyl-3-pyrrolidinol according to the present invention, which has the constitution mentioned above, can produce optically active N-benzyl-3-pyrrolidinol efficiently on a commercial scale. The optically active N-benzyl-3-pyrrolidinol obtained according to the present invention is of high optical purity and is an important intermediate for the production of medicinal copounds such as β-lactam antibiotics and dihydropyridine compounds.

What is claimed is:

1. A method of producing optically active N-benzyl-3-pyrrolidinol which comprises a step of obtaining a reaction mixture by treating N-benzyl-3-pyrrolidinone with cells or a culture of a microorganism, or a material derived therefrom, and a step of recovering optically active N-benzyl-3-pyrrolidinol from the reaction mixture, wherein said microorganism is a microorganism belonging to the genus Dipodascus, Micrococcus, Komagataella or Ogataea.

2. A method of producing optically active N-benzyl-3-pyrrolidinol which comprises a step of obtaining a reaction mixture by treating N-benzyl-3-pyrrolidinone with cells or a culture of a microorganism, or a material derived therefrom, and a step of recovering optically active N-benzyl-3-pyrrolidinol from the reaction mixture, wherein said microorganism is a microorganism belonging to the species *Dipodascus tetrasperma, Debaryomyces hansenii var. hansenii, Cryptococcus albidus var. albidus, Pichia membranaefaciens, Rhodsporidium toruloides, Trichosporon fermentans, Komagataella pastoris, Ogataea polymorpha, Zygosaccharomyces bailii*, or *Micrococcus luteus*.

3. The method of producing optically active N-benzyl-3-pyrrolidinol according to claim 2, wherein said microorganism is a microorganism belonging to the strain *Dipodascus tetrasperma* CBS 765.70, *Debaryomyces hansenii var. hansenii* IFO 0728, *Cryptococcus albidus var. albidus* IFO 0378, *Pichia membranaefaciens* IFO 0189, *Rhodsporidium toruloides* IFO 0413, *Trichosporonfermentans* ATCC 10675, *Komagataella pastoris* IFO 0948, *Ogataea polymorpha* IFO 1476, *Zygosaccharomyces bailii* IFO 0519 or *Micrococcus luteus* IFO 13867.

* * * * *